United States Patent [19]

Ostlund et al.

[11] Patent Number: 4,934,374
[45] Date of Patent: Jun. 19, 1990

[54] METHOD OF ANALYZING CARDIAC DATA USING CORRELATION PLOTS

[75] Inventors: Stellan Ostlund, Coral Gables, Fla.; Robert dePaola, Philadelphia, Pa.

[73] Assignee: Trustees of the University of Pennsylvania, Philadelphia, Pa.

[21] Appl. No.: 292,486

[22] Filed: Dec. 29, 1988

[51] Int. Cl.$^5$ .............................................. A61B 5/04
[52] U.S. Cl. .................................... 128/695; 128/710
[58] Field of Search ........... 128/695, 696, 710, 413.02, 128/413.04, 413.05, 413.06

[56] References Cited

U.S. PATENT DOCUMENTS

| | | | |
|---|---|---|---|
| 3,442,264 | 5/1969 | Levitt | 364/413.06 |
| 4,697,597 | 10/1987 | Sanz et al. | 364/413.06 |
| 4,700,712 | 10/1987 | Schmid | 364/413.06 |
| 4,812,976 | 3/1989 | Lundy | 364/413.06 |

*Primary Examiner*—Francis Jaworski
*Assistant Examiner*—George Manuel
*Attorney, Agent, or Firm*—Woodcock, Washburn, Kurtz, Mackiewicz & Norris

[57] ABSTRACT

A method of converting apparently chaotic time series data to a visual texture which, when displayed, can be really analyzed empirically. Correlation plots of vectors derived from time series of heartbeat intervals are displayed in color, to reveal useful information. The invention is particularly useful in a hospital cardiac environment, where subtle changes in cardiac rhythm can, with the method of this invention, provide evidence of abnormal cardiac functions.

4 Claims, 2 Drawing Sheets

METHOD OF ANALYZING CARDIAC DATA USING CORRELATION PLOTS

The present invention relates to novel methods of processing, displaying and viewing data to study complex dynamical systems. Improvements of correlation diagrams and patterns are presented as a novel way of viewing cardiac data.

BACKGROUND OF THE INVENTION

It is widely believed that complex dynamical systems possess considerably more predictability than is apparent by a naive mathematical or statistical analysis. For instance, it is known that simple mathematical recursions can lead to extraordinary complex behavior leading to time series that pass many tests for being random.

There are many situations in nature when there are patterns (correlations) present, a well as randomness. The eye is a sensory organ particularly well adapted to recognize such structure in complex patterns in the presence of noise. By processing data to uncover underlying patterns, and then displaying the processed data, the observers may then see patterns which lead to a more precise fundamental description of the data, and ultimately aid in understanding the underlying dynamical system and the physiology.

Methods of generating and displaying time series data have been disclosed. The present invention is an improvement of a method disclosed by D. Ruelle, *Proceedings of the Santa Barbara Conference on Non-Linear Dynamics*, Aug. 1987.

SUMMARY OF THE INVENTION

It is an object of the present invention to provide methods of displaying patterns in physiological data so they present the data in a better form to be visually observed.

It is a specific object of the present invention to provide an improved display of time series cardiac data in a form better adapted to assist in evaluation and diagnosis.

In a preferred embodiment of the invention, a computer terminal is used to analyze in real time heartbeat interval data from a patient. Vectors are composed of successive series of time delays of a single variable, i.e. successive heartbeat intervals. A correlation plot is generated and displayed, where the pixels on the screen represent measured lengths of differences of vectors and each difference is represented by a color varying from yellow to red. Thus, the gray levels of the vectors are translated on a scale of 0–255 to different colors, revealing dramatic patterns which can be correlated with physiological events.

In a hospital environment, these correlation plots provide a tool which unmasks subtle cardiac rhythms and presents dramatic patterns and textures which are more readily recognizable. By correlating these patterns with physiological information, a bank of knowledge will be generated which can provide a valuable tool, complimentary to EKG analysis, which can be used to diagnosis cardiac conditions and to provide an indication of a situation needing attention in a cardiac ICU.

DETAILED DESCRIPTION OF THE INVENTION

Figure 1:
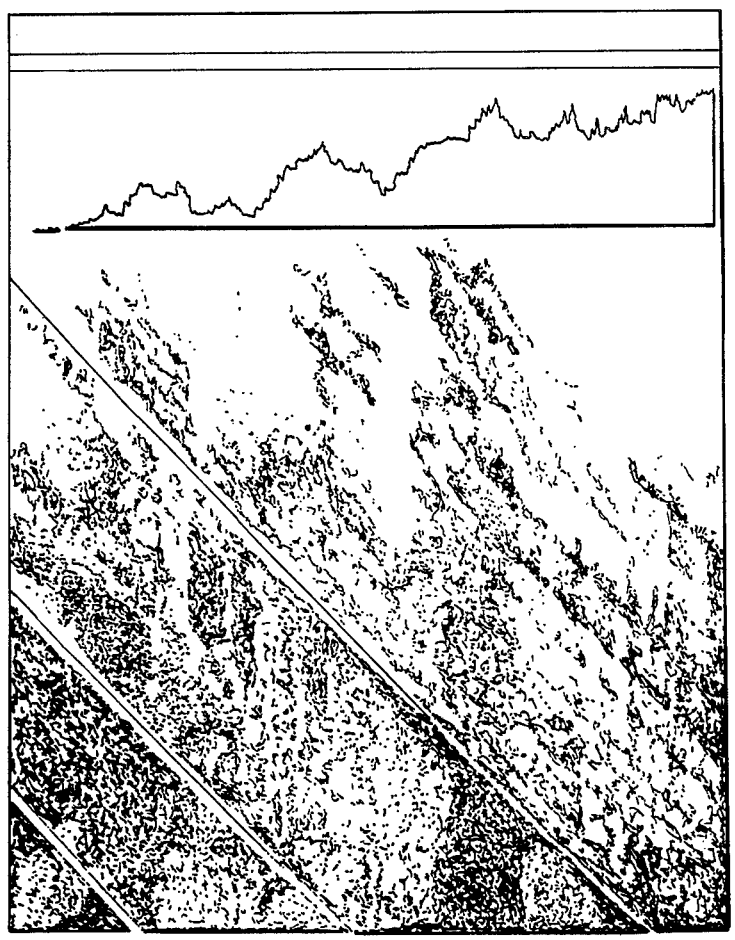
FIG. 1 represents a correlation plot of the heartbeat of a neo-natal pig, the data being taken while the pig was being mechanically respirated before heart transplant surgery.
Figure 2:
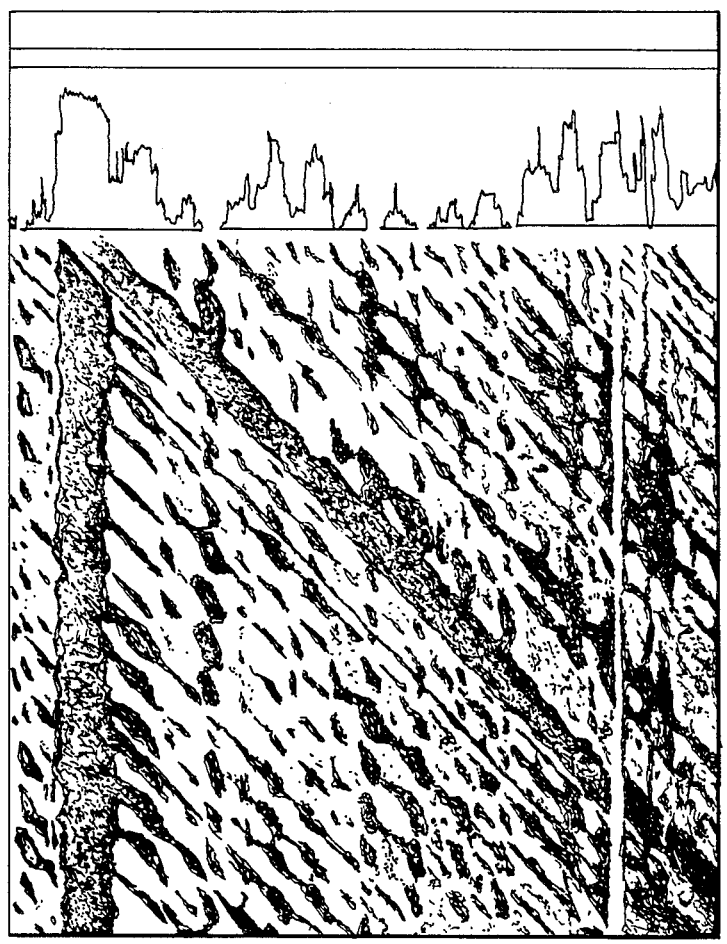
FIG. 2 is a correlation plot for the same pig after transplant.

The present invention demonstrates that cardiac data is complex but fundamentally non-random. There is a random component in the data, but no assumptions about the magnitude of this noise are made. Since the underlying physiologic mechanisms are not well controlled, it is not possible to write down an ab-initio model which accurately describes the system.

According to the method presented by Ruelle, $I_n$ denotes the differences of measured successive heartbeat intervals, measured in milliseconds, the cardiac dynamical system evolves in a finite-dimensional subspace of the essentially infinite dimensional space available. The dimension of this space of minimal dimension is called $D_{min}$. A projection of these data into essentially any space composed of at least $D_{min}$ dimensions will then be substantially related to any other projection via a change of coordinates, and hence will yield essentially the same picture independent of the precise definitions of the coordinates onto which the data are projected. A vector is then composed of successive time delays of a single variable, allowing the exploration of the embedding of the dynamical system in a highdimensional space from a single time series.

Data is made into a collection of vectors $X_k$, where k runs over the entire length of data:

$$X_k = (I_k, I_{k+1}, \ldots I_{k+D-1})$$

where $D > D_{min}$.

Ruelle suggested that a two dimensional picture can be made by choosing an arbitrary number, say $\epsilon$, and making a 2-D picture representing the proximity of pairs of vectors X and X'. A point (k,k') in the 2-D plane is marked black if $[X_k - X_{k'}]$ is less than $\epsilon$. If $D > D_{min}$, a pattern might result which the eye may recognize, even if it may still be difficult to describe quantitatively. The pattern results from the fact that if two points are nearby in this D dimensional space, the pair of subsequent points should also be nearby.

The present invention represents an improvement of Ruelle's idea and uses a color graphics terminal to plot a color value to represent the proximity of pairs of vectors $X_k$ and $X_{k'}$. We have chosen the x-axis to correspond to the ordinal number k and the vertical axis to correspond to k' so that the color at point (k,k') encodes $[\overline{X}HD\ k - \overline{X}HD\ k']$. The color "white" implies a small value of the norm, the color blue corresponds to average correlations and reddish corresponds to unusually poor correlated data.

If a system were completely random, the correlation plot would appear to be filled by a uniformly random collection of dots, giving an essentially featureless picture. The presence of simple periodic behavior in the dynamics would result in evenly spaced parallel strips along the line x=y. And, more complex behavior leads to more complex patterns.

In the preferred embodiment, the data is obtained by measuring the interval between successive heartbeats of a patient. For example, in monitoring a human patient, successive intervals would be measured at 815 ms; 820 ms; 825 ms; etc. These successive heartbeat intervals, or time delays of a single variable, represent the basic time series. From this, in practicing the method of this invention an n dimensional vector is obtained. This is done in a computer, using well-known mathematical techniques, by taking the raw time series data and excerpting series of successive interval values. For example, consider N to define the number of heartbeat intervals for which data is obtained. If $N=1,000$ (meaning that 1,001 successive heartbeats have been monitored), an n-dimensional vector can be obtained from this time series where n can be any value up to N. Taking $n=3$, any three successive values of the heartbeat interval can be taken to form a three-dimensional vector. Using successive elements of the time series to generate vectors, the number V of vectors that can be so obtained equals $N-n+1$. Having obtained the vectors, these vectors can be compared with each other to determine the measure of difference, or correlation. Thus, imagining the three-dimensional vector in x, y, z space, the value of the difference of each pair of vectors derived from the time series can be determined by well-known mathematical techniques.

In the practice of this invention, the vector differences are plotted on a two-dimensional color display. In plotting the two-dimensional color representation of the measured differences, or vector correlations, each pixel located at position i, j represents the determined difference of the i and j vectors. The difference is transformed into color by classifying the differences into 256 levels, and generating a color corresponding to each determined difference level.

The data to which the method of the present invention was applied are time series generated by measuring the interval between successive heartbeats in a neo-natal pig.

The data shown in FIG. 1A and 1B represent the correlation plot of the heartbeat of a neo-natal pig. The data were taken while the pig was being mechanically respirated before heart transplant surgery. The correlation plot for the same pig after the transplant is shown in FIG. 1B. The heartbeat interval was measured to 19 bits accuracy by triggering an interval timer on the QRS feature of the EKG trace.

It has been found that two features dominate the correlation plots. The narrow white stripes represent the influence of the breathing cycle on the heartbeat interval. The breathing cycle is correlated with the apparent heartbeat interval both by changing the morphology of the EKG on which the interval timer is triggering and by the presence of neural stimulation of the heart which is in phase with the respiratory cycle. Secondly, the long-time structure shows a slow evolution and fluctuation of the cardiac rhythm. This is an indication of the coupling between the heart and the vascular bed, whose oscillations are known to oscillate with a period consistent with this time scale (80 heartbeat intervals).

The present invention discloses new methods of analyzing cardiac data. Displaying cardiac rhythms in this manner is a useful clinical tool for investigating arrhythmias and other disorders which generate abnormal cardiac rhythms. A major advantage of this method in comparison to EKG analysis or spectral (e.g. Fourier) Analysis, is that a slow evolution of cardiac rhythms give dramatic changes in these patterns, whereas these slow changes may be difficult to observe either in an ordinary EKG or via spectral analysis. Finer patterns than those we preliminarily identified are also thought to be useful in understanding cardiac behavior. This technique may be of ultimate benefit in understanding the dynamics of physiological or other systems more precisely.

What is claimed is:

1. A process for converting and displaying physiological data so that it can be more readily analyzed empirically, comprising:
    (a) obtaining a time series composed of successive time delays of a single variable;
    (b) generating a vector from said time series;
    (c) generating a collection of vectors from respective such time series;
    (d) determining the proximity or correlation of pairs of said respective vectors and generating a color value corresponding to each such proximity; and
    (e) providing a color-coded display of said determined proximities, representing a correlation plot.

2. The process as described in claim 1, wherein said time series comprises successive heartbeat intervals.

3. The process as described in claim 2, wherein each vector is an n-dimensional vector derived from n successive heartbeat intervals of said time series.

4. The process as described in claim 1, comprising comparing a said display with other displays in accordance with claim 1, and diagnosing a patient's cardiac condition as a function of said comparison.

* * * * *